(12) United States Patent
Biancolillo et al.

(10) Patent No.: US 10,180,406 B2
(45) Date of Patent: Jan. 15, 2019

(54) SEMICONDUCTOR GAS SENSOR DEVICE AND MANUFACTURING METHOD THEREOF

(71) Applicant: STMicroelectronics S.r.l., Agrate Brianza (IT)

(72) Inventors: Pasquale Biancolillo, Pedara (IT); Angelo Recchia, Fasano (IT); Pasquale Franco, Reggio Calabria (IT); Antonio Cicero, Palermo (IT); Giuseppe Bruno, Paterno (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 0 days.

(21) Appl. No.: 15/808,408

(22) Filed: Nov. 9, 2017

(65) Prior Publication Data
US 2018/0074000 A1 Mar. 15, 2018

Related U.S. Application Data

(62) Division of application No. 14/725,842, filed on May 29, 2015, now abandoned.

(30) Foreign Application Priority Data

Jun. 30, 2014 (IT) ................ MI2014A1186

(51) Int. Cl.
*H01L 29/739* (2006.01)
*G01N 27/18* (2006.01)
(Continued)

(52) U.S. Cl.
CPC ............ *G01N 27/18* (2013.01); *B81B 7/02* (2013.01); *B81B 7/04* (2013.01); *G01N 33/0027* (2013.01);
(Continued)

(58) Field of Classification Search
CPC ............ G01N 27/18; G01N 33/0027; B81B 2201/02; B81B 2201/0292; B81B 7/02; B81B 7/0077; B81B 7/0061
See application file for complete search history.

(56) References Cited

U.S. PATENT DOCUMENTS 3,801,972 A    4/1974  Ho Kim et al.
4,457,954 A *  7/1984  Dabill .................... G01N 27/16
                                                      422/97
(Continued)

FOREIGN PATENT DOCUMENTS

EP    2431737 A1    3/2012
GB     864293  *    3/1961
(Continued)

OTHER PUBLICATIONS

Machine translation, Kanzaki, Japanese Pat. Pub. No. JP H11-74545, translation date: May 14, 2018, Espacenet, all pages.*
(Continued)

*Primary Examiner* — Victoria K Hall
(74) *Attorney, Agent, or Firm* — Crowe & Dunlevy (57) ABSTRACT

A semiconductor gas sensor device includes a first cavity that is enclosed by opposing first and second semiconductor substrate slices. At least one conducting filament is provided to extend over the first cavity, and a passageway is provided to permit gas to enter the first cavity. The sensor device may further including a second cavity that is hermetically enclosed by the opposing first and second semiconductor substrate slices. At least one another conducting filament is provided to extend over the second cavity.

14 Claims, 10 Drawing Sheets

(51) Int. Cl.
*G01N 33/00* (2006.01)
*B81B 7/02* (2006.01)
*B81B 7/04* (2006.01)
*G01N 30/66* (2006.01)

(52) U.S. Cl.
CPC ... *B81B 2201/02* (2013.01); *B81B 2201/0278* (2013.01); *G01N 30/66* (2013.01)

(56) References Cited

U.S. PATENT DOCUMENTS

| | | | | |
|---|---|---|---|---|
| 5,048,336 | A * | 9/1991 | Sugihara | G01N 27/18 338/35 |
| 5,345,213 | A * | 9/1994 | Semancik | B01L 7/54 257/253 |
| 5,356,786 | A * | 10/1994 | Heller | C12Q 1/002 204/157.15 |
| 5,451,371 | A * | 9/1995 | Zanini-Fisher | G01N 27/16 204/424 |
| 2004/0070006 | A1 * | 4/2004 | Monty | G01N 27/127 257/200 |
| 2008/0016943 | A1 * | 1/2008 | Arnold | G01N 30/468 73/23.39 |
| 2008/0315333 | A1 * | 12/2008 | Combi | B81B 7/0061 257/415 |
| 2009/0035184 | A1 * | 2/2009 | Koda | G01N 27/16 422/94 |
| 2013/0311108 | A1 * | 11/2013 | Stetter | G01N 27/00 702/22 |
| 2014/0260546 | A1 * | 9/2014 | Chen | G01N 27/128 73/31.06 |

FOREIGN PATENT DOCUMENTS

| | | | | |
|---|---|---|---|---|
| GB | 892530 | * | 3/1962 | |
| JP | S60-194347 | * | 10/1985 | ............. G01N 27/12 |
| JP | H11-74545 | * | 3/1993 | ............. H01L 31/00 |
| JP | 2004-61244 | * | 2/2004 | ............. G01N 27/16 |
| JP | 2010185867 A | | 8/2010 | |
| WO | WO 91/02243 | * | 2/1991 | ............. G01N 27/16 |

OTHER PUBLICATIONS

Machine translation, Abe, Japanese Pat. Pub. No. JP 2004-61244, translation date: May 14, 2018, Espacenet, all pages.*
Abstract, Yoshitake, Japanese Pat. Pub. No. JP S60-194347, print date: May 14, 2018, Derwent, all pages.*
Italian Search Report and Written Opinion for IT MI2014A001186 dated Mar. 5, 2015 (8 pages).
Sorge S et al: "Fully Integrated Thermal Conductivity Sensor for Gas Chromatography Without Dead Volume," Sensors and Actuators A, Elsevier Sequoia S.A., Lausanne, CH, vol. 63, No. 3, Dec. 1997, pp. 191-195, XP027083722.

* cited by examiner

SEMICONDUCTOR GAS SENSOR DEVICE AND MANUFACTURING METHOD THEREOF

CROSS REFERENCE TO RELATED APPLICATIONS

This application is a divisional of U.S. application for patent Ser. No. 14/725,842 filed May 29, 2015 which claims priority from Italian Application for Patent No. MI2014A001186 filed Jun. 30, 2014, the disclosures of which are incorporated by reference.

TECHNICAL FIELD

The present disclosure relates to a semiconductor gas sensor device and the manufacturing method thereof.

BACKGROUND

The thermal conductivity detector (TCD) is well known in the state of the art. A TCD is an environmental sensor device widely used for the measurement of the amount of gas in the environment. The operation is based on the fact that each gas has an inherent thermal conductivity and a filament (thermal resistor) changes its temperature as a function of the amount of gas that surrounds it. The most appropriate sensing element shape is that of a thin finger suspended, for which the temperature of the central part can locally reach even values of several hundred degrees. The feature that the finger is totally suspended allows for enhancing the amount of heat exchange with the gas in which it is immersed. The warming effect of the suspended finger is induced through an electrical stress of the sensor, for example by means of the flow of current through the finger. The sensor is able to better discriminate the gases whose conductivity is much different than normal air (roughly $N_2$ (79%), $O_2$ (19%), $CO_2$ (0.04%), plus other gases with negligible quantities: for example the CO is a few ppm).

When a current flows through the finger, the value of the resistance of the finger changes. The measurement of the resistance value allows for measuring the conductivity of the gas mixture which depends on the molar fraction of the gas of interest.

However, it is difficult in principle to discriminate which is the gas mainly responsible for the conductivity variation of the mixture of gas. For example, $CO_2$ has a lower thermal conductivity than dry air, therefore if its percentage increases inside the mixture, this will raise the temperature of the sensor with a consequent increase of the value of the measured resistance.

The TCD sensor operates in accordance with the thermodynamic equilibrium among heat generated by the current flow, heat exchange with the material of which the sensor is made (e.g., polysilicon crystalline), and heat exchange with the gas mixture surrounding it. The ambient temperature determines the equilibrium value of the sensor in standard dry air. To take into account and compensate for the variation of ambient temperature, a Wheatstone bridge could be used as the sensor structure. The reference branches of the bridge are of the same nature and positioned in the vicinity of the sensor so as to be sensitive to the same way to changes in ambient temperature, with the difference that will not be exposed to the mixture of gas as the sensor.

The Relative Humidity (RH) is the amount of water vapor (gas) present in the environment compared to a saturated environment in the same conditions of pressure and temperature. The thermal conductivity of water vapor is much larger than the dry air therefore an increase in relative humidity produces a lowering of the temperature of the sensor with a consequent reduction of the value of the measured resistance. The contribution of the RH value of the measured resistance could be 1/10 compared to the change of resistance in the presence of $CO_2$, therefore, this is a parameter to measure and correct. Typically the correction is made by means of a dedicated sensor for the measurement of the RH.

In view of implementation of space saving and low power consumption, a demand exists to further reduce the size of gas detectors for measuring the concentration of gas. In recent years, gas detection elements with greatly reduced sizes have been developed by the use of MEMS (Micro-Electro-Mechanical System) technology (also called the micromachining technique). A gas detection element formed by use of MEMS technology is configured such that a plurality of thin films are formed in layers on a semiconductor substrate (e.g., a silicon substrate). Examples of such a gas detection element include a thermal-conductivity-type gas detection element. The thermal-conductivity-type gas detection element has a heat-generating resistor and utilizes the phenomenon that, when the heat-generating resistor is energized and generates heat, heat is conducted to the gas. The conduction of heat causes a change in temperature of the heat-generating resistor and thus a change in resistance of the heat-generating resistor. On the basis of the amount of the change, the gas is detected. In the thermal-conductivity-type gas detection element, the resistance of the heat-generating resistor varies with the type or concentration of the gas.

SUMMARY

One aspect of the present disclosure is to provide a semiconductor gas sensor device of simple architecture with respect to the known ones.

One aspect of the present disclosure is a semiconductor gas sensor device comprising: one doped semiconductor substrate of a first semiconductor slice, a first insulating layer placed above said doped semiconductor substrate, a part of at least one first cavity formed inside said first insulating layer and said doped semiconductor substrate and extending inside said doped semiconductor substrate to a prefixed depth, at least one conductive filament placed over said part of the at least one first cavity in a bridge way, a conductive metal layer placed at the ends of at least one filament for contacting it, another doped semiconductor substrate of a second semiconductor slice, said another doped semiconductor substrate comprising the other part of the at least one first cavity and being placed above said doped semiconductor substrate of the first semiconductor slice so as to form and close said at least one first cavity, said another doped semiconductor substrate comprising at least one hole in correspondence of the first cavity for the inlet of gas to detect.

BRIEF DESCRIPTION OF THE DRAWINGS

For a better understanding of the present disclosure, a preferred embodiments thereof are now described, purely by way of non-limiting examples and with reference to the annexed drawings, wherein.

DETAILED DESCRIPTION

Figures 1A, 1B, 2A:
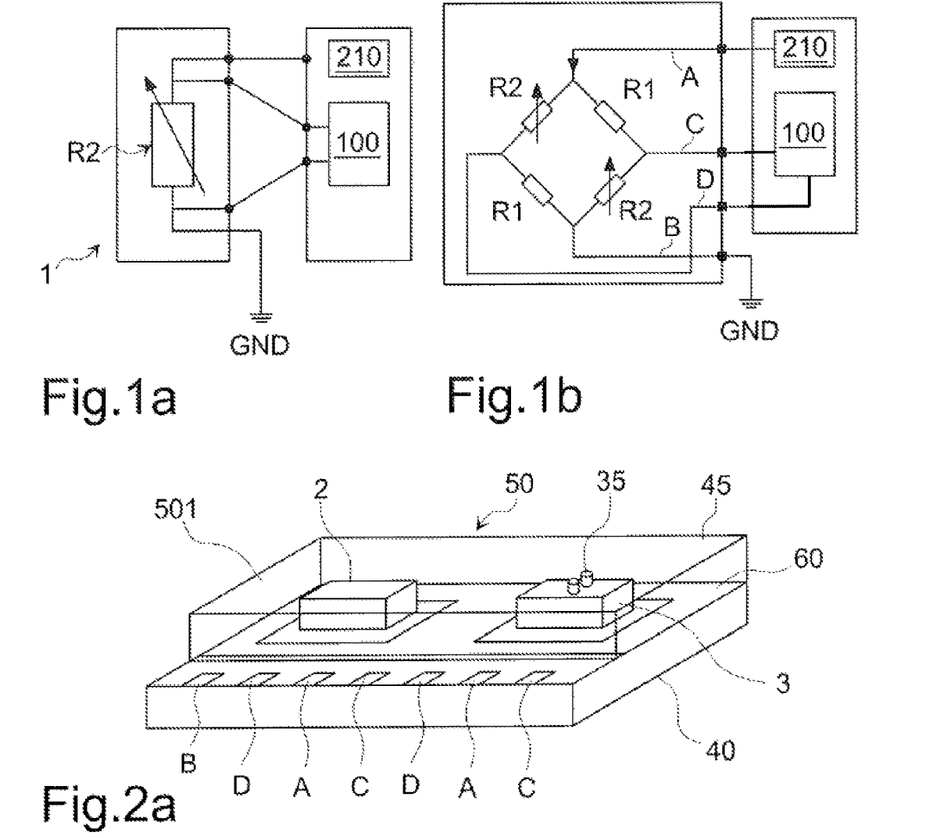
FIG. 1A shows a block diagram of a measurement apparatus comprising a measurement device and an integrated gas sensor device according to a first embodiment of the present disclosure.
FIG. 1B shows a block diagram of a measurement apparatus comprising a measurement device and an integrated gas sensor device according to a second embodiment of the present disclosure.
FIG. 2A shows a schematic layout of the integrated semiconductor gas sensor device according to a second embodiment of the present disclosure.

FIG. 1A and FIG. 1B show a block diagram of a measurement apparatus comprising a gas sensor device 1 or a gas sensor device 50 according respectively to a first and a second embodiment of the present disclosure and a measurement device 100.

Figure 20:
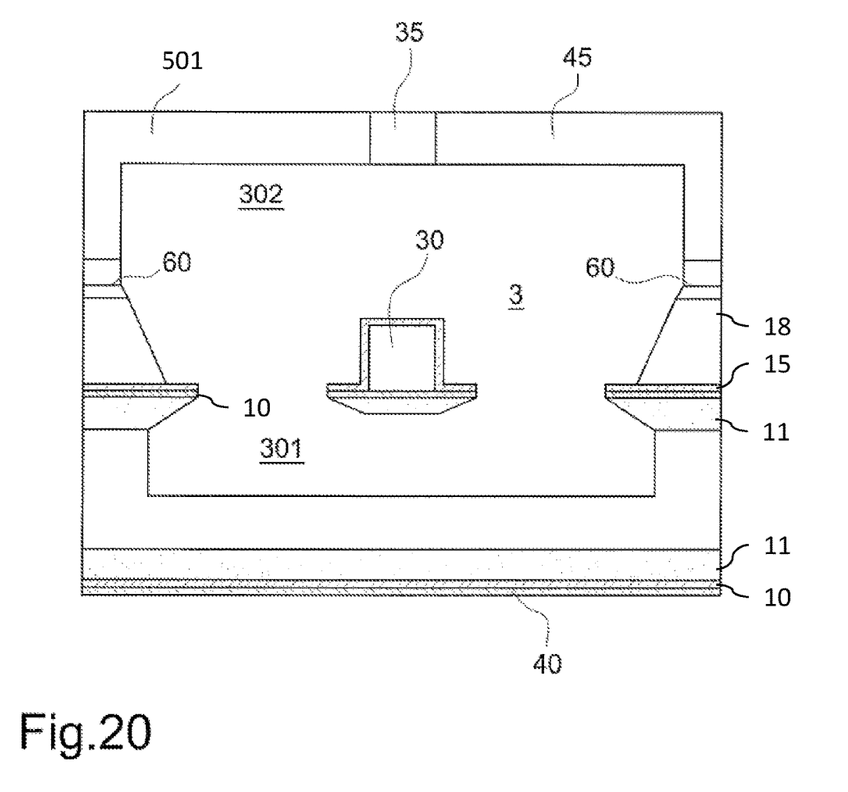
FIG. 20 is a cross sectional view more in detail of the semiconductor gas sensor device according to the first embodiment of the present disclosure.

According to a first embodiment of the present disclosure, the integrated semiconductor gas sensor device 1 comprises at least one variable resistor R2 exposed to the gas (FIG. 1A). The terminals of the resistor R2 are connectible with a variable current generator 210 and ground GND; also the terminals of the resistor R2 are connectable to the measurement device 100 able to measure the voltage across the variable resistor R2. According to the present disclosure the resistor R2 is formed in a semiconductor substrate wherein at least a cavity 3 is formed which is coated by silicon but is open to the outside by means of one hole 35 so that the cavity 3 is exposed to the gases (FIG. 20). The resistor R2 is formed in the cavity 3 by means of a suspended filament 30 preferably made of polysilicon; the filament 30 is arranged in a bridge way. The sensitivity of the resistor R2 depends on the resistivity of the filament 30, where reducing the resistivity increases the sensitivity; for example a filament in polysilicon with size of 50×1×1 microns can be used.

According to a second embodiment of the present disclosure, the integrated semiconductor gas sensor device is preferably a Wheatstone bridge 50 including a couple of reference resistors R1 and a couple of variable resistors R2 exposed to the gas (FIG. 1B); the use of a Wheatstone bridge allows for minimizing the dependence on the ambient temperature. The four connecting nodes A-D of the terminals of the resistances R1 and R2 of the Wheatstone bridge 50 are connectible respectively with a variable current or voltage generator 210, to ground GND and to the measurement device 100 able to receive the voltage signal at the output of the Wheatstone bridge 50.

Figure 2B:
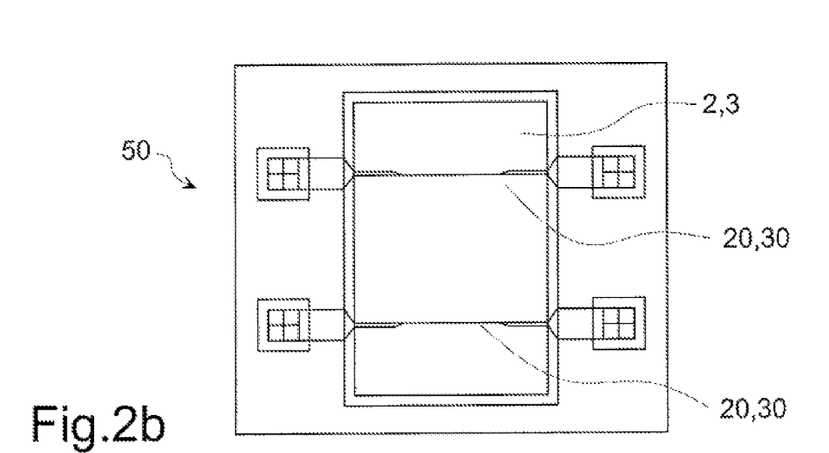
FIG. 2B shows a schematic layout of the sensing elements of the integrated semiconductor gas sensor device in FIG. 2A.

According to the present disclosure the Wheatstone bridge 50 is formed in a semiconductor substrate wherein two cavities 2 and 3 are formed which are both hermetically coated by silicon but wherein the only cavity 3 is open to the outside by means of two holes 35 so that the cavity 3 is exposed to the gases (FIG. 2A). The couple of reference resistors R1 are formed in the cavity 2 by means of suspended filaments 20 while the couple of resistors R2 are formed in the cavity 3 by means of suspended filaments 30 (FIG. 2B); the filaments 20 and 30 are formed preferably in polysilicon. The sensitivity of the Wheatstone bridge 50 depends on the resistivity of the filaments 30, where reducing the resistivity increases the sensitivity; for example a filament in polysilicon with size of 50×1×1 microns can be used.

Figure 3:
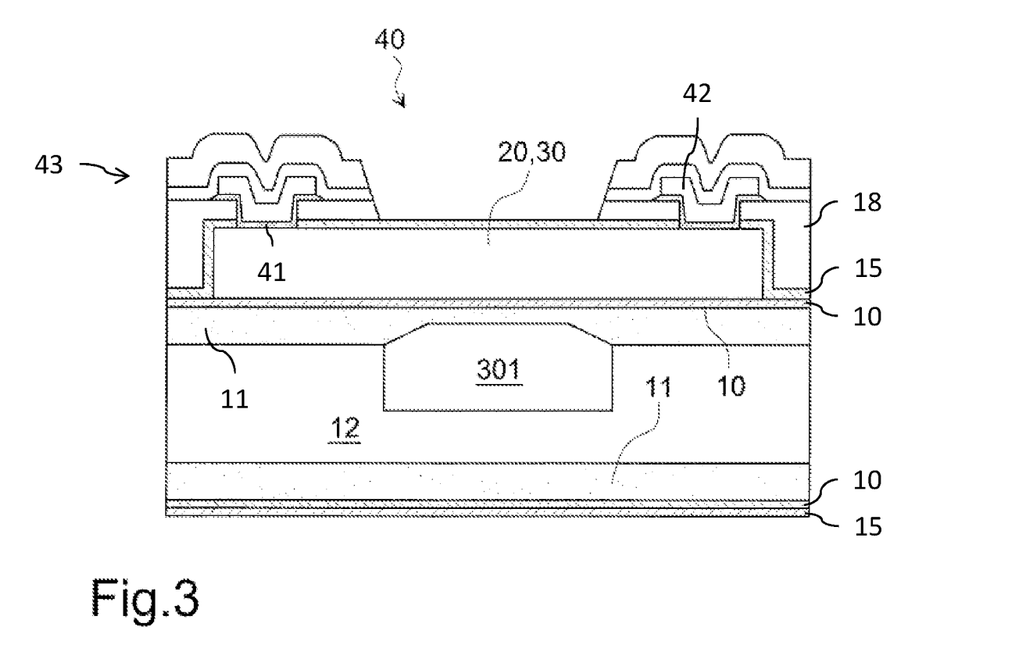
FIGS. 3 and 4 are cross sectional views of a part of the semiconductor gas sensor device according to the first embodiment of the present disclosure.
Figure 4:
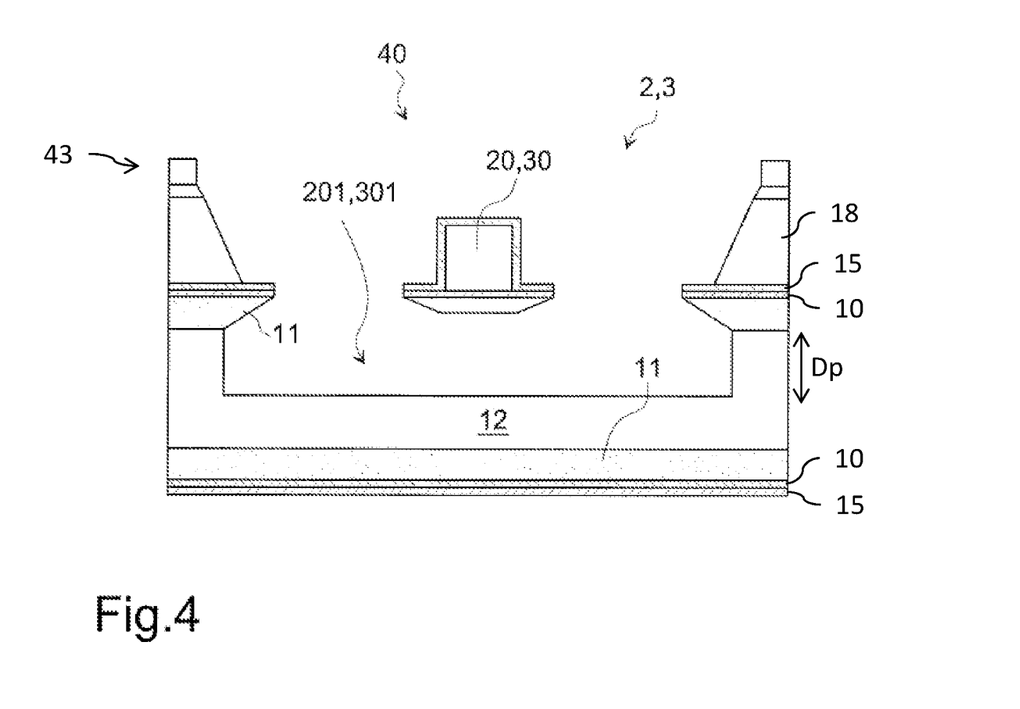

FIGS. 3, 4 and 20 show cross sectional views of a part of the integrated gas sensor device 1 formed in a semiconductor substrate; the sections show a doped semiconductor substrate 12 of a first semiconductor slice 40, preferably a silicon slice preferably of the n type, and at least one insulating layers 10, 11 placed above said doped semiconductor substrate, but preferably a succession of a nitride 10 and oxide 11 layers are placed over the semiconductor substrate 12.

A lower part 301 of the cavity 3 is formed inside said doped semiconductor substrate 12 and the at least one insulating layer 10, 11 and extends inside said doped semiconductor substrate to a prefixed depth Dp, for example of 10 microns; at least one conductive filament 30, preferably made in polysilicon, is placed inside the cavity 3 in a bridge way for forming the resistor R2, that is the conductive filament 30 is suspended over the lower part 301 of the cavity 3. In the case of the integrated gas sensor device using a Wheatstone bridge 50, two filaments 30 are placed inside the cavity 3 in a bridge way for forming the resistors R2 and a lower part 201 of another cavity 2 is formed inside said doped semiconductor substrate 12 and the at least one insulating layer 10, 11 and extends inside said doped semiconductor substrate to the prefixed depth Dp, for example of 10 microns; two conductive filaments 20, preferably made in polysilicon, are placed inside said lower part 201 of the cavity 2 in a bridge way for forming the resistors R1, that is the conductive filaments 20 are suspended over the lower part 201 of the cavity 2. The conductive filaments 20, 30 are placed preferably at a distance of 100 micrometers.

A second insulating layer 15, preferably a nitride layer, is placed above and around the at least one conductive filament 30 except in the contact zones at the ends of the filament; a conductive metal layer 41 is placed on the ends of the filament for contacting them. In the case of the integrated gas sensor device using a Wheatstone bridge 50, the second insulating layer 15 is placed above and around said conductive filaments 30, 20 except in the contact zones at the ends of each filament; a conductive metal layer 41 is placed on the ends of the filaments for contacting them so that the first pair of conductive filaments 20 represent the reference resistors R1 of the Wheatstone bridge 50 while the second pair of conductive filaments 30 represent the variable resistors of the Wheatstone bridge 50.

A doped semiconductor layer 501 of a second semiconductor slice 45 which comprises the upper part 302 of the at least one first cavity 3 is placed above the first semiconductor slice 40 as to form the cavity 3 and to close said cavity 3; the doped semiconductor layer 501 presents at least one hole 35 for the inlet of gas to detect. In the case of the integrated gas sensor device 50, the doped semiconductor layer 501 comprises the upper part 302 of the cavity 3 and the upper parts 202 of the cavity 2; the doped semiconductor layer 501 is placed above the first semiconductor slice 40 as to form the cavities 2 and 3 and to hermetically close the cavity 2 and close the cavity 3. The doped semiconductor layer 501 present at least one hole 35 but preferably two holes 35 for the inlet of gas to detect in the cavity 3.

Figure 5:
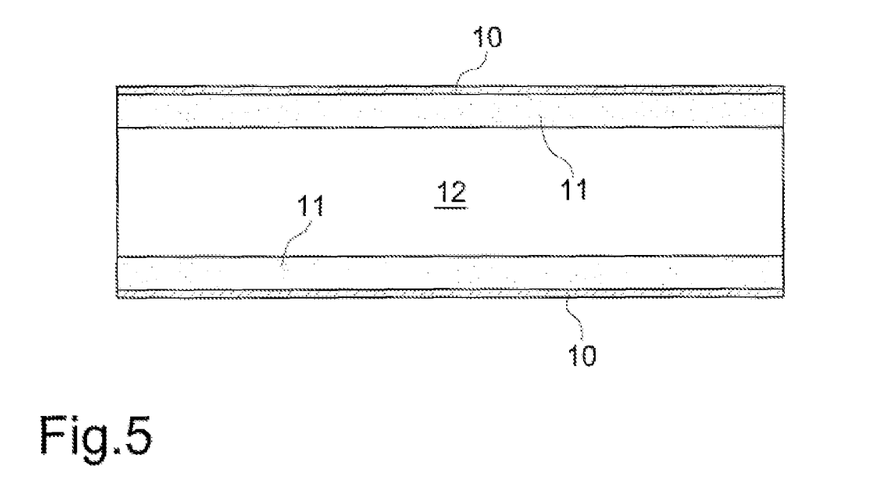
FIGS. 5-17 show the manufacturing process of the part of the semiconductor gas sensor device in FIGS. 3 and 4.

The process for the formation of the semiconductor gas sensor device 1 comprises a thermal oxidation of a part of a silicon substrate 12 of a first silicon slice 40, preferably an n type silicon substrate, for forming silicon oxide layers 11 over and under the substrate 12 with a thickness of 0.5 microns and a deposition of insulating layers 10, for example nitride layers with a thickness of 1000 angstrom, over the oxide layers 11 (FIG. 5) formed over and under the silicon substrate 12 with a thickness of 725 microns.

Figure 6:
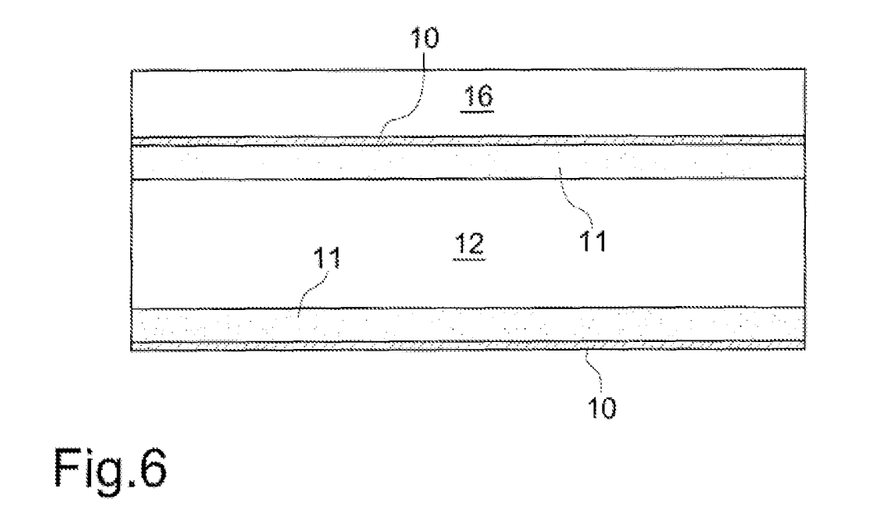

Successively a deposition of a polysilicon with a resistivity of 1.35 mΩ×cm occurs over the upper nitride layer 10 for forming a conductive layer 16, preferably a polysilicon layer 16, with a thickness of 1 micron (FIG. 6).

Figure 7:
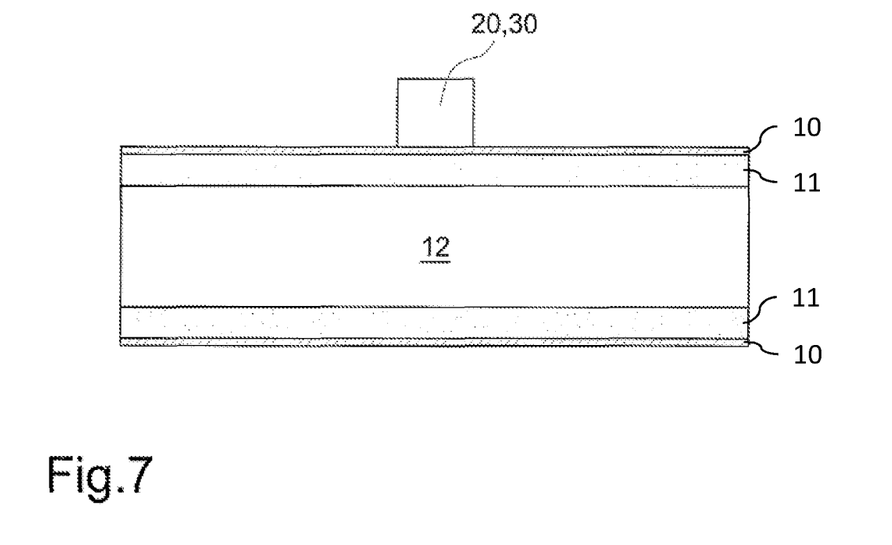

The filament 30 or the filaments 20, 30 in the case of forming the Wheatstone bridge 50 are then defined from the conductive layer 16 as is shown in FIG. 7; this is obtained by placing a lithographic mask over the conductive layer 16 and successively effectuating a dry etching.

Figure 8:
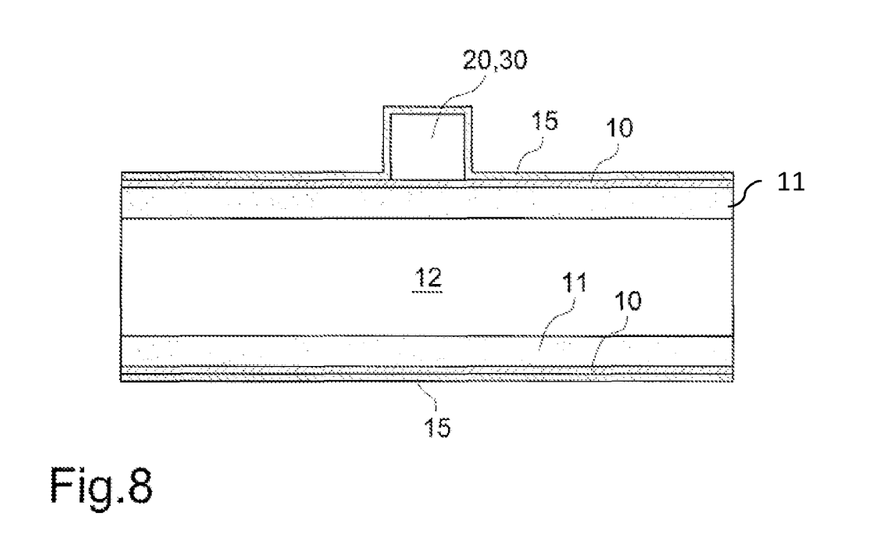
Figure 9:
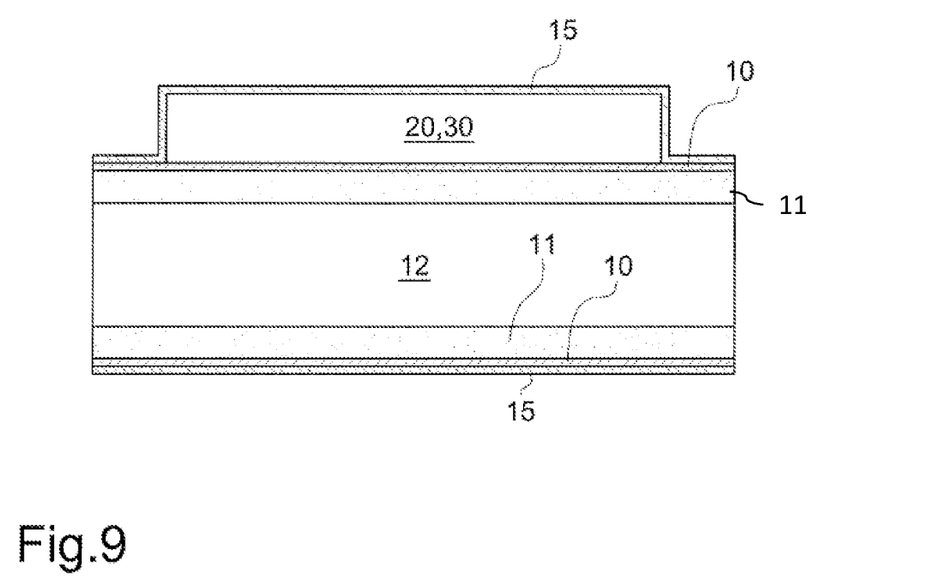

In the next step an insulating layer 15, preferably a nitride layer, is grown above and around the polysilicon filament 30 or the polysilicon filaments 20, 30 in the case of forming the Wheatstone bridge 50 and over the nitride layer 10 (FIG. 8, 9 wherein the section across the filaments and the section along the filaments are respectively shown) and an activation step of the dopant of the polysilicon layer 16 is effectuated.

Figure 10:
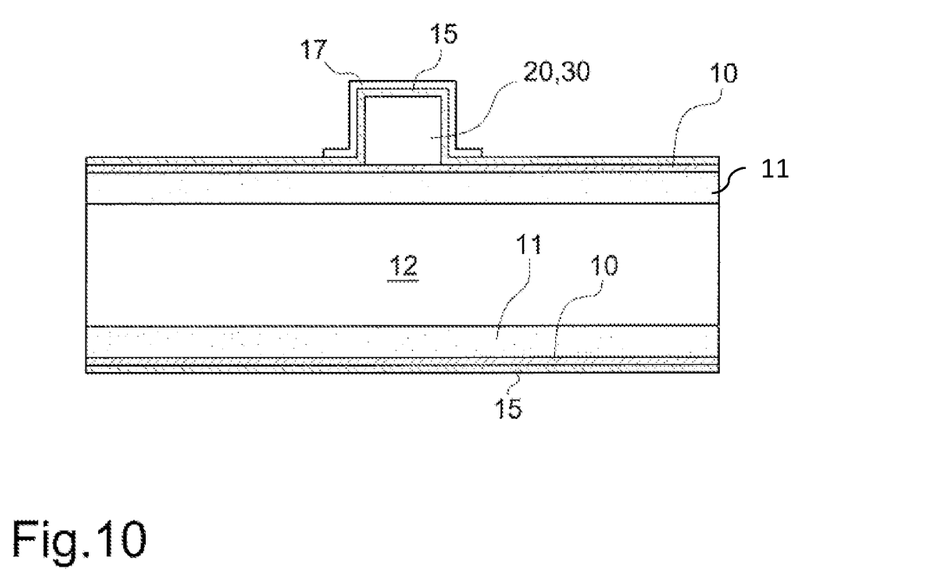

Preferably, a successive RF sputtering deposition technique of metal, for example a palladium, is effectuated over the nitride layer 15 for forming the palladium layer 17 which is defined by placing a lithographic mask over the conductive palladium layer 17 and a successive etching is effectuated so that the palladium layer 17 is maintained only over and around the polysilicon filament 30 or the polysilicon filaments 20, 30 in the case of forming the Wheatstone bridge 50 (FIG. 10). The palladium layer 17 is optional and allows protecting the polysilicon filaments from weathering and making the polysilicon filaments controllable by process and stable over the time.

Figure 11:
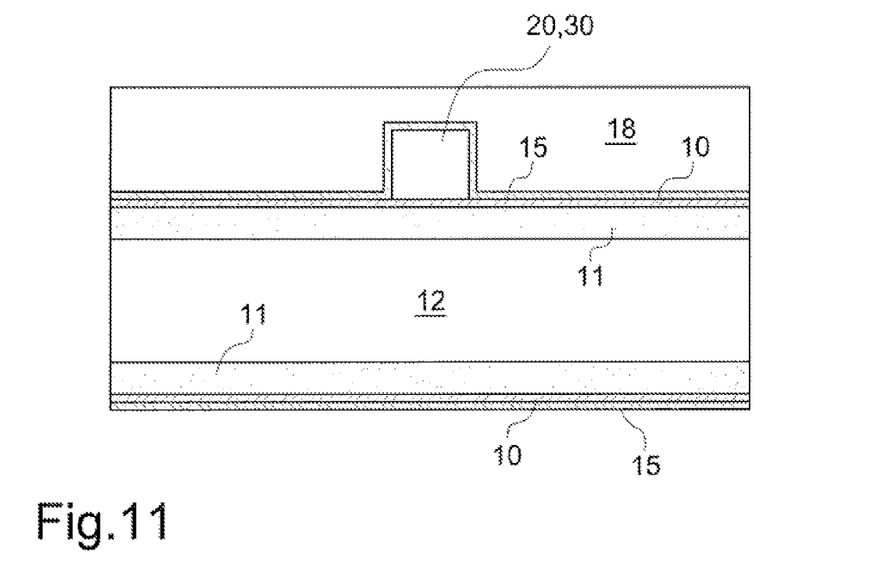

Successively a silicon oxide deposition, preferably a tetraethylorthosilicate (TEOS) silicon oxide, over the nitride layer 15 for forming a silicon oxide layer 18 is effectuated (FIG. 11). The thickness of the silicon oxide layer 18 is preferably of 3000 angstroms over the nitride layer 15 placed above the polysilicon filament 30 or the polysilicon filaments 20, 30 in the case of forming the Wheatstone bridge 50.

Figure 12:
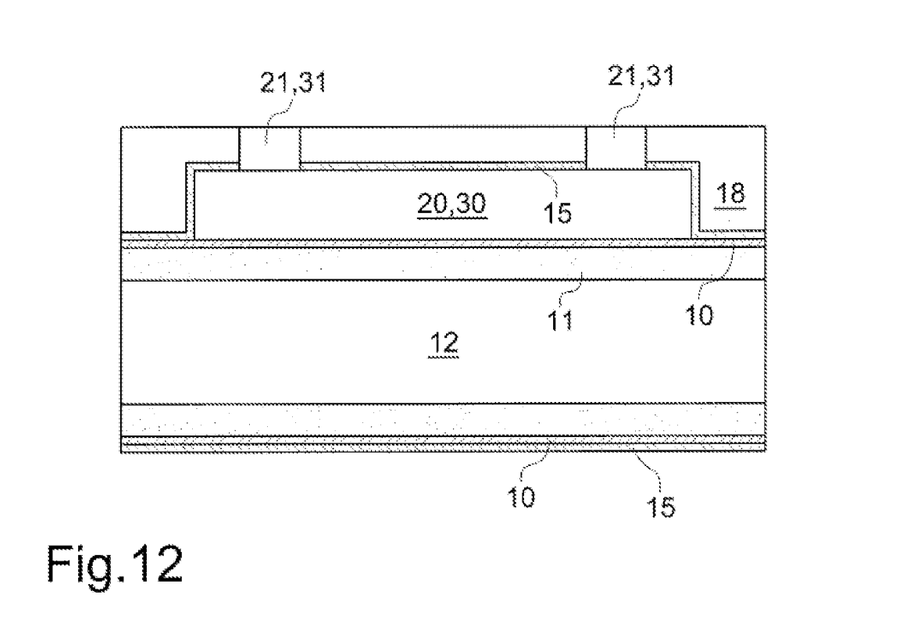

The next step is a definition of the contact zones 31 of the filament 30 or the contact zones 21, 31 (in the case of forming the Wheatstone bridge 50) of the filaments 20, 30 by placing a lithographic mask over the layer 18 and successively effectuating a dry etching (FIG. 12) of the layers 15 and 18.

Figure 13:
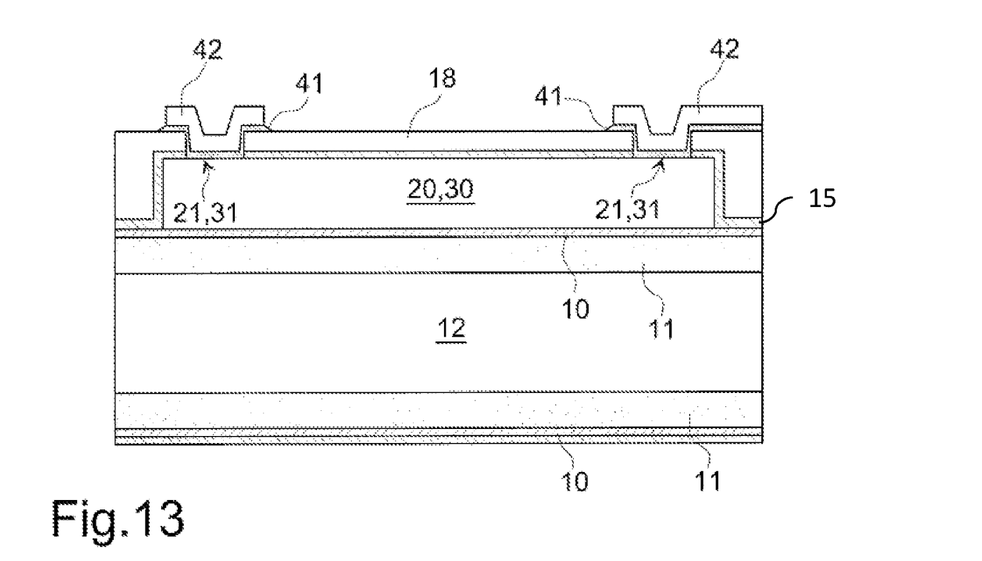

A RF sputtering deposition technique of metal, preferably Titanium and Aluminum, is typically used for the formation of the metal layer 41 (FIG. 13). A successive definition of the metal contacts is effectuated by placing a lithographic mask over the layer 41 and successively effectuating a dry etching (FIG. 13) of the layer 41. Resist strips 42 are placed above the metal layer 41.

Then, a deposition of a further silicon oxide layer 43 occurs, preferably by means of two LPCVD depositions (low pressure chemical vapor deposition), with a thickness of preferably of 6000 angstroms, to obtain a total oxide layer with a thicknesses preferably of 9000 and 19000 angstroms over the nitride layer 15.

Figure 14:
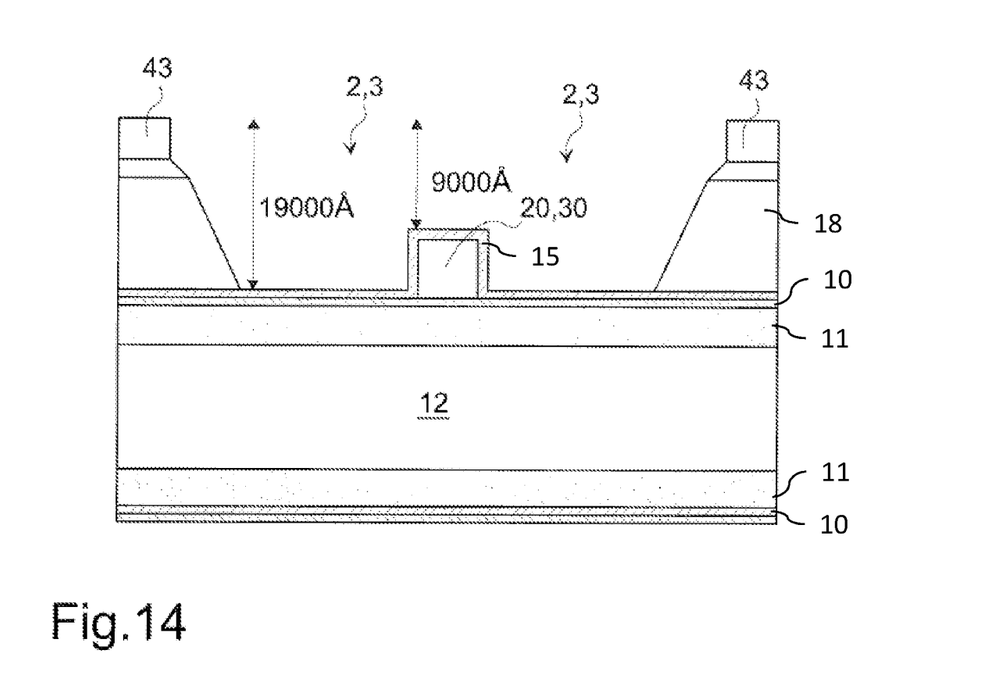
Figure 15:
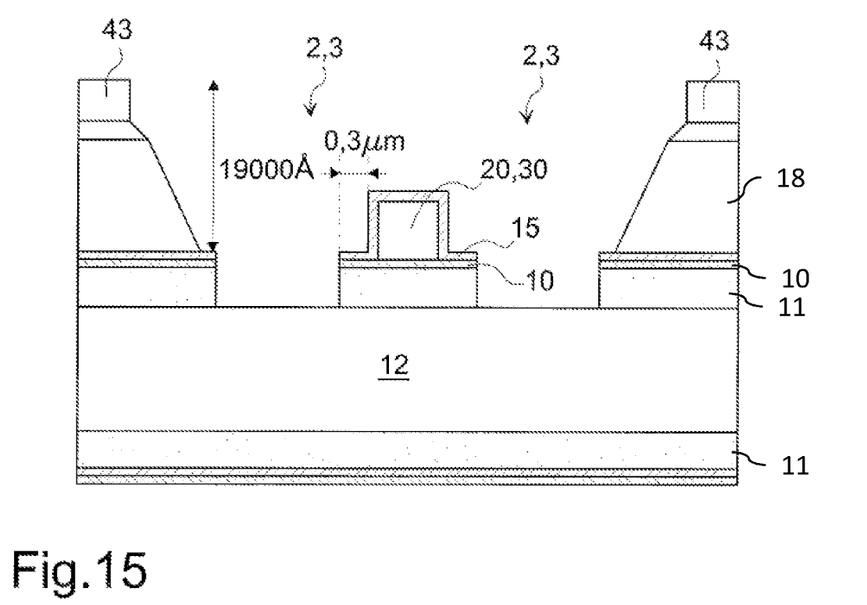
Figure 16:
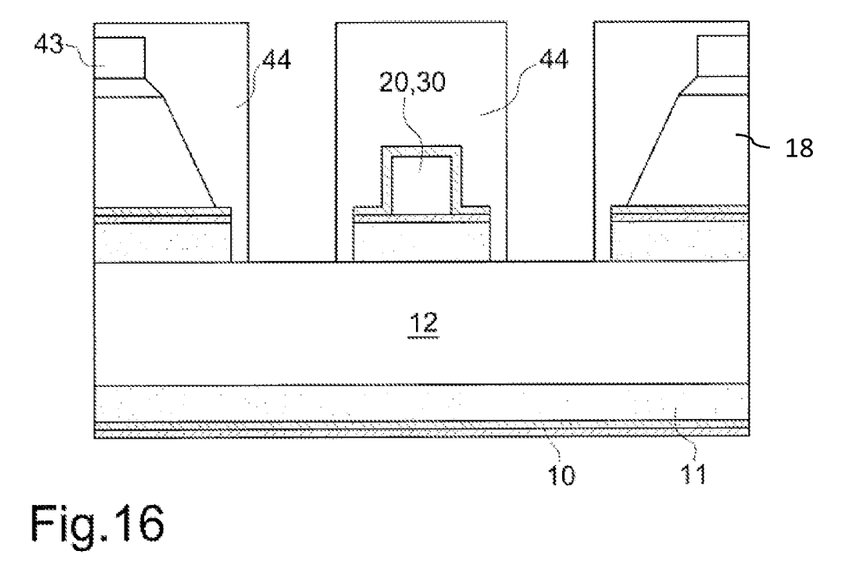
Figure 17:
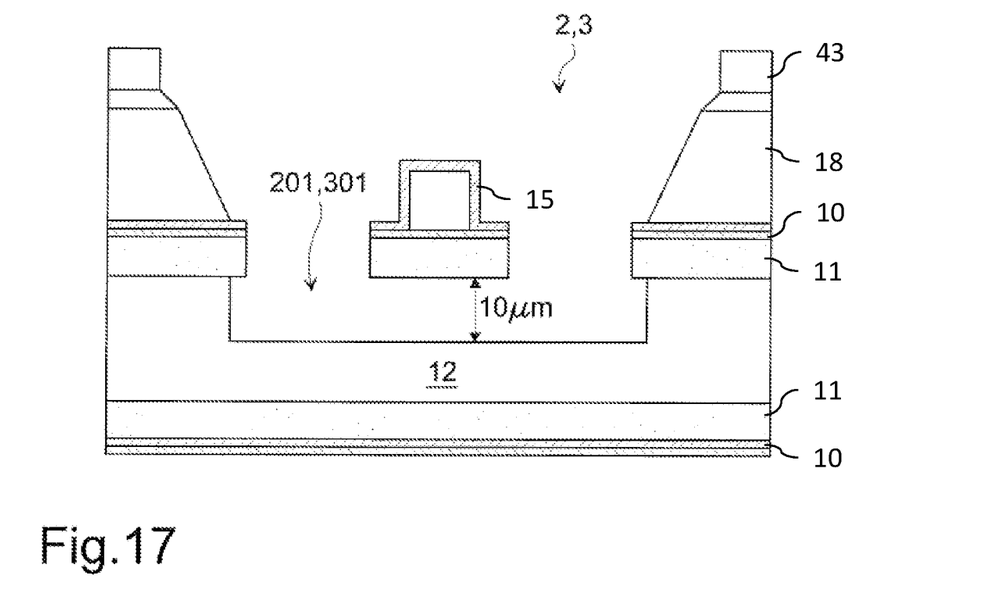

Successively the formation of the lower part 301 of the cavity 3 or the lower parts 201, 301 of the cavities 2 and 3 (in the case of forming the Wheatstone bridge 50) occur. This is obtained by placing a lithographic mask over the layer 43 and successively effectuating a wet etching to arrive to the nitride layer 15 in the area around the filament 30 or each filament 20, 30 (FIG. 14), placing another lithographic mask over the nitride layer 15 and successively effectuating a dry etching of the nitride layers 15, 10 and the oxide layer 11 to arrive to the substrate 12 in the area around the filament 30 or each filament 20, 30 preferably at a distance of 0.3 microns from the polysilicon filament 30 or each polysilicon filament 20, 30 (FIG. 15) and placing a resist mask 44 over the substrate 12 so that the resist layer is placed at a distance of 0.8 microns from the polysilicon filament 30 or each polysilicon filament 20, 30 and 0.5 microns from the oxide layer 11 (FIG. 16) and successively effectuating an anisotropic and isotropic dry etching of the substrate 12 of a depth Dp=10 microns (FIG. 17) to etch even the portion of the silicon substrate 12 under the from the polysilicon filament 30 or the polysilicon filaments 20, 30.

Successively another dry etching of the oxide layer 11 occurs to arrive at the device in FIGS. 3, 4.

Figure 18:
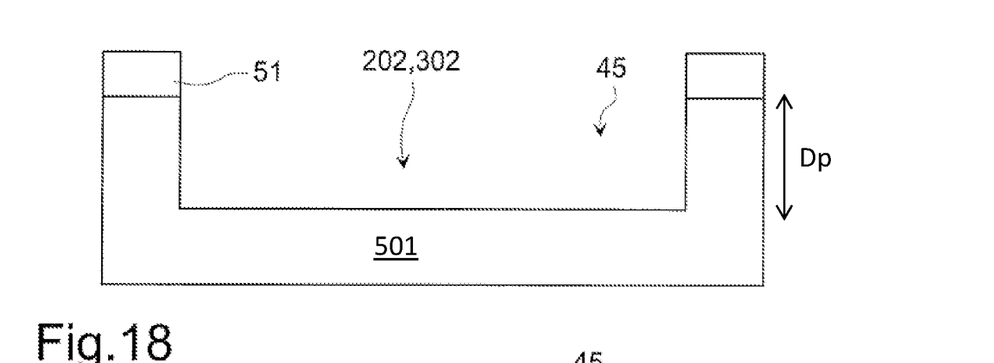
FIGS. 18-19 show the manufacturing process of the other part of the semiconductor gas sensor device according to the first embodiment of the present disclosure.

The process for the formation of the semiconductor gas sensor device comprises placing a resist mask 51 on a semiconductor substrate 501 of a second semiconductor slice 45, preferably a n type silicon substrate, to define the upper part 302 of the cavity 3 or the upper parts 202, 302 of the cavities 2, 3 and successively effectuating an anisotropic and isotropic dry etching of the substrate 501 for a depth Dp=10 microns (FIG. 18) to form the upper part 302 of the cavity 3 or the upper parts 202, 302 of the cavities 2, 3.

Figure 19:
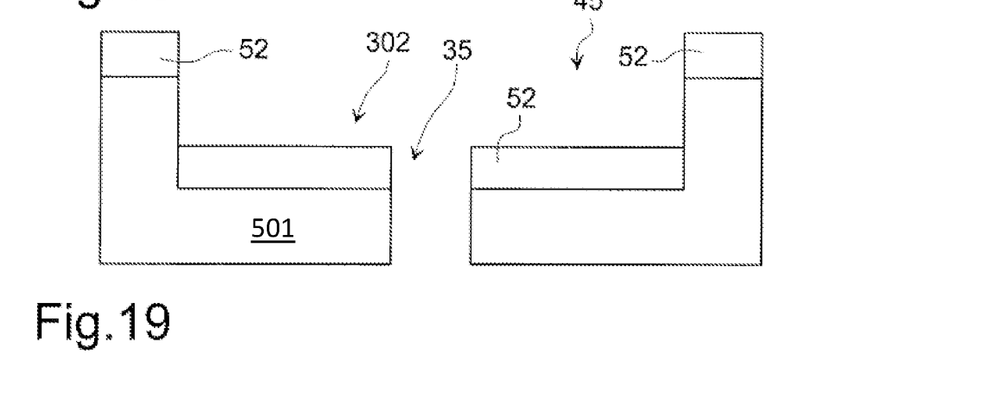

The process comprises even placing a resist mask 52 on a silicon substrate 501 after the definition of the upper part 302 of the cavity 3, to define at least one hole 35 only in the upper part 302 of the cavity 3 and successively effectuating an anisotropic and isotropic dry etching of the substrate 501 to form the hole 35 in the upper part 302 of the cavity 3 (FIG. 19).

The first 40 and second 45 semiconductor slices are joined together so that the lower part 301 corresponds to the upper part 302 or the lower parts 301, 201 correspond respectively to the upper parts 202, 302; in this way the only cavity 3 or both the cavities 2 and 3 are formed. Preferably the first 40 and second 45 semiconductor slices are joined together by using an adhesive 60 such as glass frit or dry resist (FIG. 20).

The invention claimed is:

1. A method for manufacturing a semiconductor gas sensor device, comprising:
   forming a doped semiconductor substrate of a first semiconductor slice,
   forming a first insulating layer above said doped semiconductor substrate,
   forming a first part of at least one first cavity inside said first insulating layer and said doped semiconductor substrate so that said first part of at least one first cavity extends inside said doped semiconductor substrate to a first depth,
   forming at least one conductive filament over said first part of the at least one first cavity in a bridge way,
   forming a first metal layer at first and second ends of the at least one conductive filament for making electrical contact,
   forming a second insulating layer on the at least one conductive filament between the first and second ends,
   forming a second metal layer, insulated from said first metal layer, on said second insulating layer between the first and second ends, forming another doped semiconductor substrate of a second semiconductor slice, forming a second part of the at least one first cavity with said another doped semiconductor substrate, forming at least one hole in correspondence of said second part of the at least one first cavity for the inlet of gas to detect, and placing the second semiconductor slice above said first semiconductor slice so as to form and close said at least one first cavity.

2. The method according to claim 1, with respect to the first semiconductor slice, further comprises:

forming parts of the first cavity and a second cavity inside said first insulating layer and said doped semiconductor substrate so that said parts of the first and second cavities extend inside said doped semiconductor substrate to the first depth, forming a first pair of conductive filaments and a second pair of conductive filaments inside said respective first and second cavities in a bridge way, said first and second pairs of conductive filaments being respectively the variable resistors and the reference resistors of a Wheatstone bridge, forming the first metal layer on the first and second ends of each conductive filament of the first and second pairs of conductive filaments for making electrical contact, forming other parts of said first and second cavities with said another doped semiconductor substrate, forming at least one hole only in correspondence of said other part of the first cavity for the inlet of gas to detect, placing the second semiconductor slice above said first semiconductor slice so as to form said first and second cavities and hermetically close the second cavity and close the first cavity.

3. The method according to claim 2, with respect to the another doped semiconductor substrate, further comprising forming two holes in correspondence only of the first cavity for the inlet of the gas to detect.

4. The method according to claim 1, wherein forming the second insulating layer comprises forming the second insulating layer positioned above and around said at least one conductive filament.

5. The method according to claim 1, wherein placing the second semiconductor slice above the first semiconductor slice comprises joining the first semiconductor slice and the second semiconductor slice using an adhesive.

6. The method according to claim 5, wherein the adhesive is glass frit.

7. The method according to claim 1, wherein the first metal layer is made of titanium or aluminum and the second metal layer is made of palladium.

8. A semiconductor gas sensor device, comprising:

a doped semiconductor substrate of a first semiconductor slice, a first insulating layer placed above said doped semiconductor substrate, a first part of at least one first cavity formed inside said first insulating layer and said doped semiconductor substrate and extending inside said doped semiconductor substrate to a first depth, at least one conductive filament placed over said first part of the at least one first cavity in a bridge way, a first metal layer placed at first and second ends of the at least one conductive filament for making electrical contact, a second insulating layer on the at least one conductive filament between the first and second ends, a second metal layer, insulated from said first metal layer, on said second insulating layer between the first and second ends, and another doped semiconductor substrate of a second semiconductor slice comprising a second part of the at least one first cavity and being placed above said first semiconductor slice so as to form and close said at least one first cavity, said another doped semiconductor substrate comprising at least one hole in correspondence of the first cavity for the inlet of gas to detect.

9. The semiconductor gas sensor device according to claim 8, wherein the first semiconductor slice comprises:

first parts of the first cavity and a second cavity formed inside said first insulating layer and said doped semiconductor substrate and extending inside said doped semiconductor substrate to the first depth, a first pair of conductive filaments and a second pair of conductive filaments placed inside said respective first and second cavities in a bridge way, said first and second pairs of conductive filaments being respectively the variable resistors and the reference resistors of a Wheatstone bridge, the first conductive metal layer being placed at the first and second ends of each conductive filament of the first and the second pairs of conductive filaments for making electrical contact, said another doped semiconductor substrate comprising second parts of the first and second cavities and being placed above said first semiconductor slice so as to form said first and a second cavities and hermetically close the second cavity and close the first cavity, said another doped semiconductor substrate comprising at least one hole in correspondence only of the first cavity for the inlet of the gas to detect.

10. The semiconductor gas sensor device according to claim 9, wherein said another doped semiconductor substrate comprises two holes in correspondence only of the first cavity for the inlet of the gas to detect.

11. The semiconductor gas sensor device according to claim 8, wherein the second insulating layer is placed above and around said at least one conductive filament.

12. The semiconductor gas sensor device according to claim 8, wherein the first and second semiconductor slices are joined together by an adhesive.

13. The semiconductor gas sensor device according to claim 12, wherein the adhesive is glass frit.

14. The semiconductor gas sensor device according to claim 8, wherein the first metal layer is made of titanium or aluminum and the second metal layer is made of palladium.

* * * * *